(12) United States Patent
Tennent et al.

(10) Patent No.: US 11,369,486 B2
(45) Date of Patent: Jun. 28, 2022

(54) ARTHROSCOPIC ANTERIOR GLENOID GUIDE

(71) Applicant: Arthrex, Inc., Naples, FL (US)

(72) Inventors: Thomas Duncan Tennent, Banstead (GB); Michael Schaumann, Munich (DE); Matthias Anderl, Eichenau (DE); Alexander James Campagnoli, Aschheim (DE)

(73) Assignee: ARTHREX, INC., Naples, FL (US)

( * ) Notice: Subject to any disclaimer, the term of this patent is extended or adjusted under 35 U.S.C. 154(b) by 130 days.

(21) Appl. No.: 16/887,282

(22) Filed: May 29, 2020

(65) Prior Publication Data

US 2021/0369469 A1    Dec. 2, 2021

(51) Int. Cl.
| | | |
|---|---|---|
| *A61F 2/46* | (2006.01) | |
| *A61B 17/17* | (2006.01) | |
| *A61F 2/28* | (2006.01) | |
| *A61B 17/00* | (2006.01) | |
| *A61B 17/04* | (2006.01) | |

(52) U.S. Cl.
CPC ........ *A61F 2/4601* (2013.01); *A61B 17/1728* (2013.01); *A61B 17/1778* (2016.11); *A61F 2/28* (2013.01); *A61B 17/00234* (2013.01); *A61B 2017/0046* (2013.01); *A61B 2017/042* (2013.01); *A61B 2017/0445* (2013.01); *A61B 2017/0453* (2013.01); *A61F 2002/2835* (2013.01); *A61F 2002/4677* (2013.01); *A61F 2002/4687* (2013.01); *A61F 2310/00359* (2013.01)

(58) Field of Classification Search
CPC ............ A61B 17/1778; A61B 17/1728; A61B 2/1684; A61B 17/1684; A61F 2/4601; A61F 2/4612
See application file for complete search history.

(56) References Cited

U.S. PATENT DOCUMENTS

| | | |
|---|---|---|
| 5,030,219 A | 7/1991 | Matsen, III et al. |
| 11,224,446 B2 * | 1/2022 | Al Shammari .... A61B 17/8897 |
| 2010/0241106 A1 | 9/2010 | Torrie |
| 2013/0023942 A1 * | 1/2013 | Wyman .............. A61B 17/8897 606/86 R |
| 2013/0066321 A1 * | 3/2013 | Mannss .............. A61B 17/1739 606/88 |

FOREIGN PATENT DOCUMENTS

| | | |
|---|---|---|
| EP | 2135566 A1 | 12/2009 |
| EP | 3057518 A1 | 8/2016 |

OTHER PUBLICATIONS

Partial European Search Report dated Oct. 29, 2021, issued in European Application No. 21176232.3.

* cited by examiner

*Primary Examiner* — Matthew J Lawson (57) ABSTRACT

Surgical constructs, assemblies and methods of tissue fixation are disclosed. An anterior glenoid guide is a cuboid block configured to be introduced via the rotator interval to lie on the anterior glenoid. The guide has an internal thread for a handle and two flanges which lie on the anterior glenoid. On the anterior face (opposite the neck of the glenoid), the guide is provided with two holes which are sized to receive a drill guide. The holes mate with slots such that the block can be removed after sutures and fixation devices are installed. The anterior glenoid guide can be an arthroscopic anterior glenoid graft guide.

11 Claims, 9 Drawing Sheets

ARTHROSCOPIC ANTERIOR GLENOID GUIDE

BACKGROUND

The present disclosure relates to the field of surgery and, more particularly, to guides for arthroscopic grafting and methods of surgical repairs.

SUMMARY

Surgical constructs, assemblies, and kits are disclosed. An anterior glenoid guide is in the form of a block configured to be introduced via the rotator interval to lie on the anterior glenoid. The guide has an internal thread for a handle and two flanges which lie on the anterior glenoid. On the anterior face (opposite the neck of the glenoid), the guide is provided with two holes which are sized to receive a drill guide. The holes mate with slots such that the block can be removed after sutures are installed. The anterior glenoid guide can be an arthroscopic anterior glenoid graft guide.

Methods of surgeries are also disclosed. In an embodiment, a method of arthroscopic grafting is conducted with an anterior glenoid guide which is configured to be employed from front to back, and not back to front like the current guides.

DETAILED DESCRIPTION

The present disclosure provides methods, surgical constructs, assemblies, kits and systems for graft formation, insertion, and positioning, for example, arthroscopic grafting of the anterior glenoid.

A surgical construct includes an anterior glenoid guide which can be introduced via the rotator interval to lie on the anterior glenoid. The anterior glenoid guide is in the form of a block provided with an internal thread for a handle and one or more flanges which lie on the anterior glenoid. On the anterior face (opposite the neck of the glenoid), the guide is provided with two holes which are sized to receive a drill guide. The holes mate with slots in the drill guide such that the block can be removed after sutures are installed. The anterior glenoid guide can be an arthroscopic graft guide. The anterior glenoid guide can be in the form of a general cuboid.

Arthroscopic grafting of the anterior glenoid (iliac crest, allograft, distal tibia, coracoid transfer) is typically undertaken by using guides inserted posteriorly and through the glenoid. The anterior glenoid guide of the present disclosure enables the simple positioning of the graft and associated graft suture anchors from an anterior portal, removing the need for additional posterior incisions. Current instrumentation such as open Latarjet instrumentation is provided with a flange that lies on the face of the glenoid and two guides for K-wires but it is designed to be inserted into a previously-drilled graft and it is only used for open surgery. The anterior glenoid guide of the present disclosure allows arthroscopic glenoid graft insertion with an anterior-based guide, i.e., a guide that can be introduced in an anterior-to-posterior manner from front to back.

An anterior glenoid guide can be an arthroscopic graft guide. An anterior glenoid guide can be introduced in an anterior-to-posterior way from front to back, and not back to front. In an embodiment, an anterior glenoid guide can be introduced arthroscopically via the rotator interval and positioned to rest on the anterior glenoid (to securely engage the anterior glenoid). An anterior glenoid guide can include a solid body in the shape of a cuboid provided with a plurality of flanges that allow positioning on an anterior face of the bone (e.g., the glenoid); an internal thread to accommodate a handle; and a plurality of through-holes or apertures that are configured and sized to engage a drill guide and to allow easy passage of fixation devices (such as screws, suture-button constructs, suture anchors, etc.) and flexible members (such as flexible strands, for example, sutures and/or suture tapes) associated with fixation devices used for graft fixation. The drill guide (an anchor drill guide) can be threaded to the anterior glenoid guide. An anterior glenoid guide can further include a hole for temporary stabilization, e.g., with a K-wire. An anterior glenoid guide can be positioned onto the anterior face of a bone (glenoid) by secure engagement of a plurality of flanges.

A surgical anterior glenoid guide can be manufactured from metals, metal alloys, non-metals, plastics, or combinations thereof. The surgical guide is a simple construct that allows precise, accurate and convenient positioning on an anterior face of a bone to be grafted (e.g., an anterior face of the glenoid). The construct minimizes the posterior insertion of instrumentation necessary for reconstruction surgeries such as open rotator cuff reconstruction (e.g., guides inserted posteriorly and through the glenoid) as well as formation of any posterior incisions. The construct of the present disclosure also allows for precise and fast placement of a graft without additional incisions and unnecessary drilling of bone tunnels through the bone to be grafted, as well as improved suture management at the repair site.

Methods of endoscopic or arthroscopic surgeries are also disclosed. An exemplary method includes inter alia the steps of: (i) arthroscopically positioning an anterior glenoid guide on an anterior face of a bone; and (ii) securing a surgical instrument to the guide. The bone can be the glenoid. The method can further include the steps of: introducing the anterior glenoid guide through an anterior arthroscopic portal and into a vicinity of the bone; engaging a plurality of bone engaging structures (flanges) of the anterior glenoid guide with one or more bone surfaces/edges of the bone; and drilling into the bone. In an embodiment, drilling can occur from one surface of the bone to another surface of the bone, to form one or more through tunnels or holes. In an embodiment, drilling can occur from one surface of the bone to another surface of the bone, to form two through tunnels spaced apart from each other and about parallel to each other. The method can further include the steps of: placing the anterior glenoid guide on a surface of a graft; securing the anterior glenoid guide to the graft; and drilling into the graft to form two through tunnels. The method can further include the step of attaching the graft to the bone (glenoid). The anterior glenoid guide can be an arthroscopic anterior glenoid guide in the shape of a solid cuboid employed for glenoid grafting in an anterior-to-posterior manner.

Figure 12:
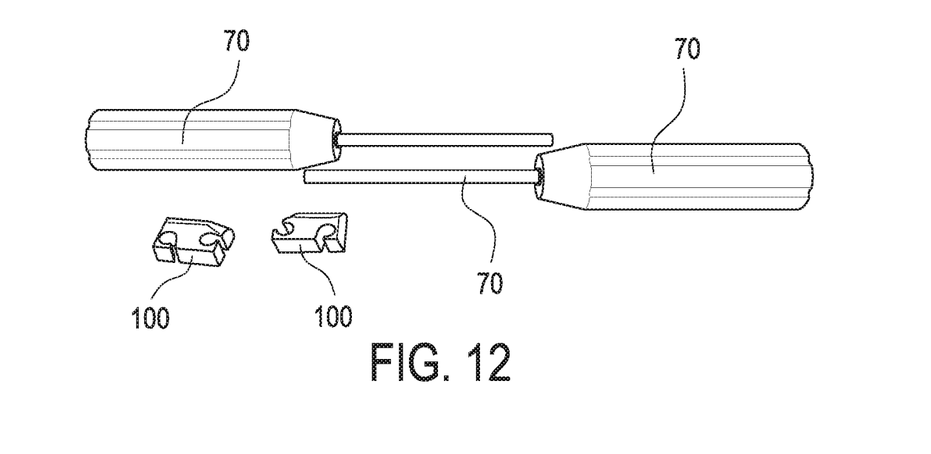
FIG. 12 illustrates a driver and guide assembly.
Figure 13:
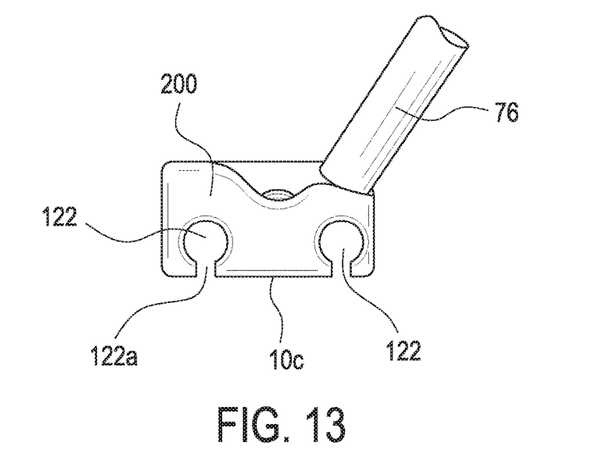
FIGS. 13-16 illustrate various views of another exemplary anterior glenoid guide.
Figure 14:
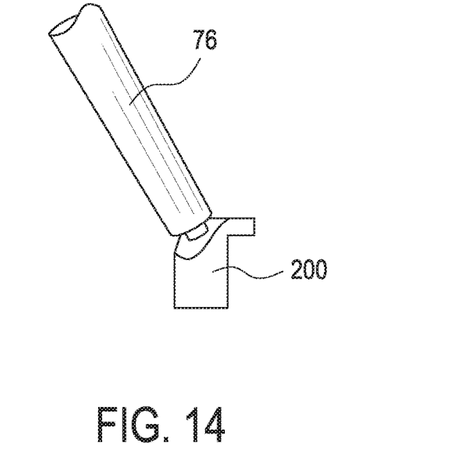
Figure 15:
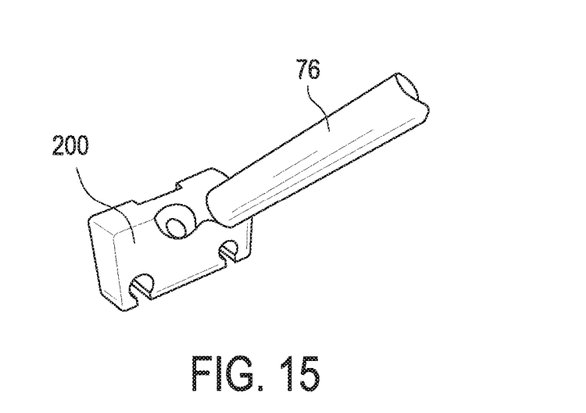
Figure 16:
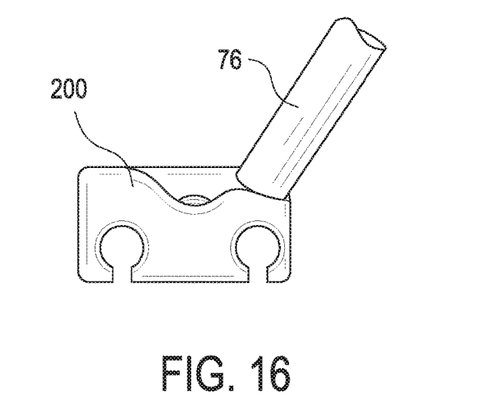
Figure 17:
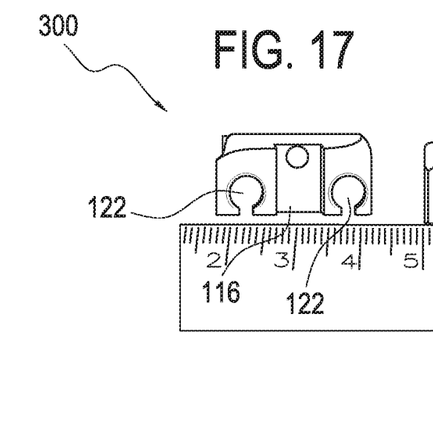
FIGS. 17-20 illustrate various views of another exemplary anterior glenoid guide.
Figure 18:
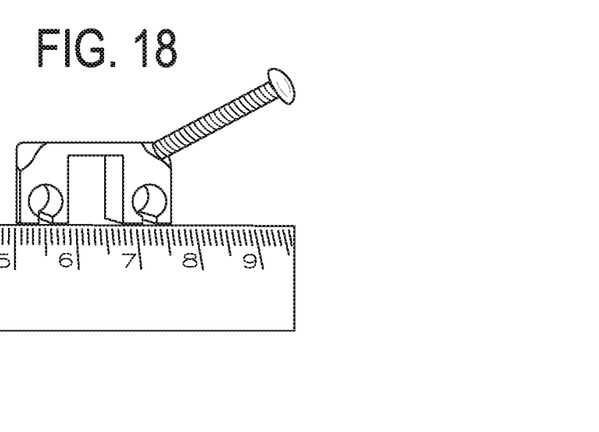
Figure 19:
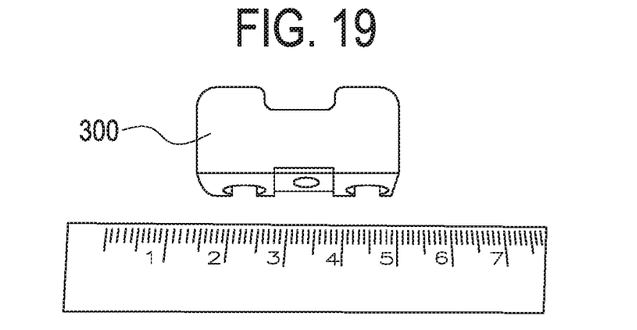
Figure 20:
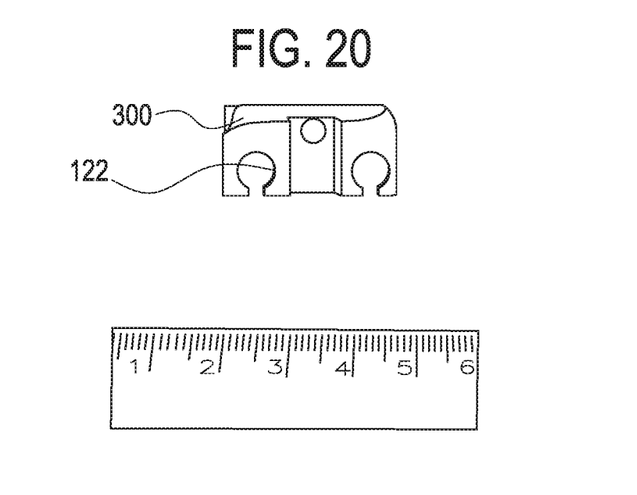
Figure 21:
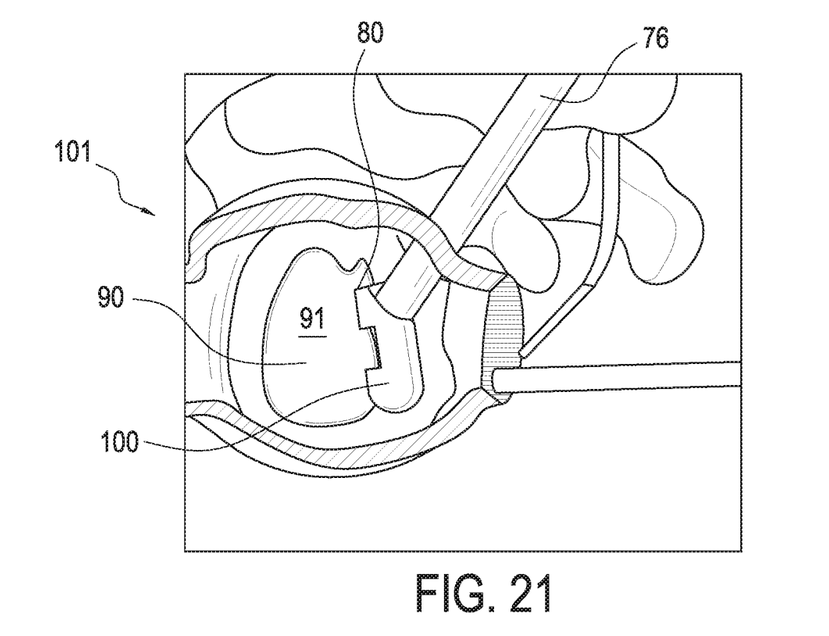
FIGS. 21 and 22 illustrate steps of an exemplary method of reconstructive surgery with the anterior glenoid guide of FIG. 5.
Figure 22:
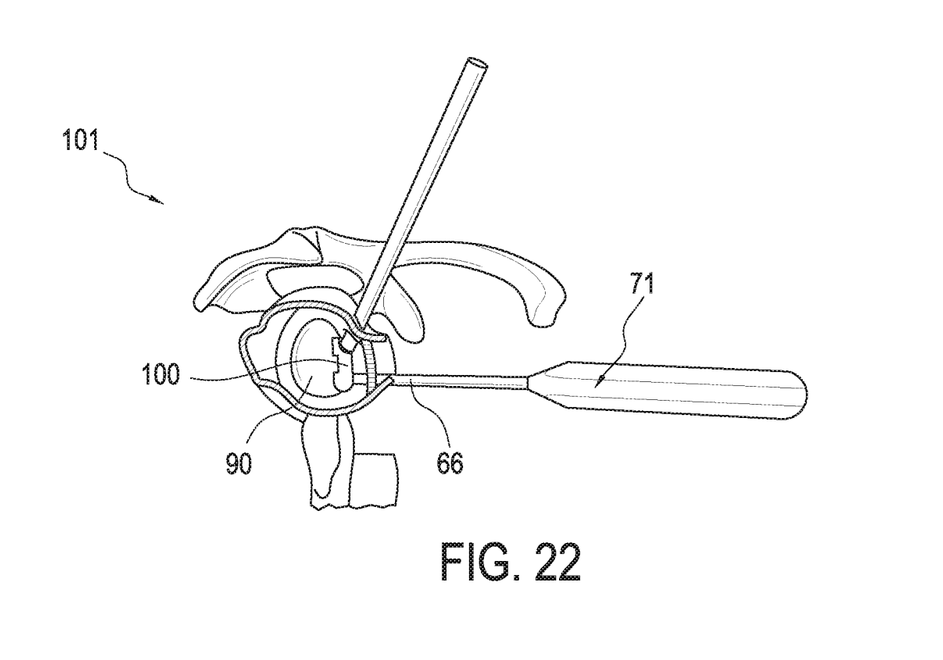
Figure 23:
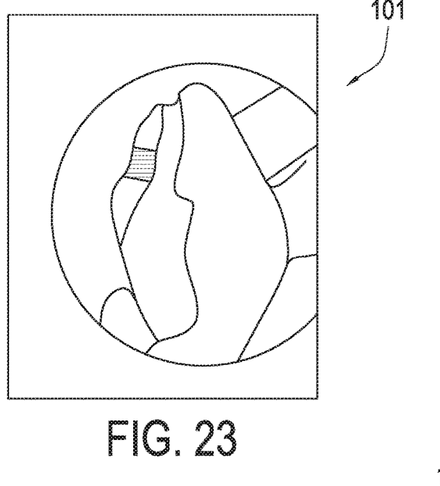
FIGS. 23-27 illustrate steps of another exemplary method of reconstructive surgery with the anterior glenoid guide of FIG. 5.
Figure 24:
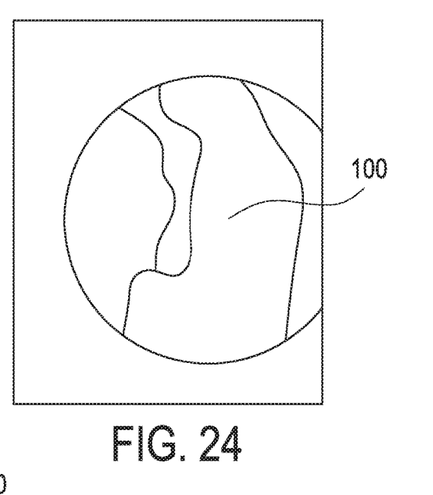
Figure 25:
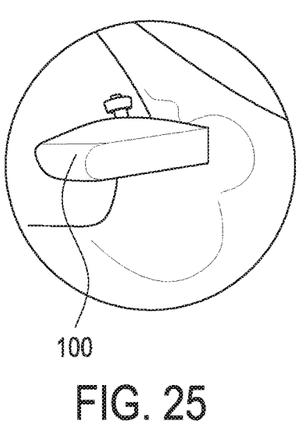
Figure 26:
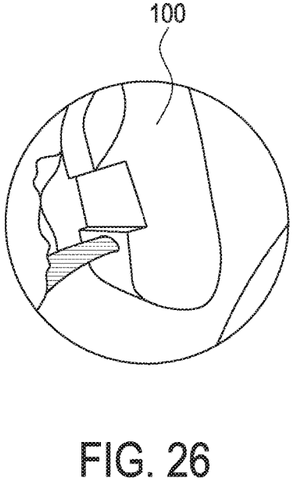
Figure 27:
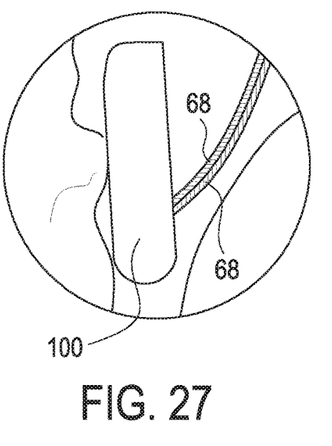

Referring now to the drawings, where like elements are designated by like reference numerals, FIGS. 1-11 illustrate various views of exemplary anterior glenoid guide 100 (arthroscopic anterior glenoid guide 100; graft guide 100; construct 100; surgical construct 100; guide 100; jig 100). FIG. 12 illustrates an assembly including the anterior glenoid guide 100 and additional instruments such as exemplary drivers. FIGS. 13-16 illustrate various views of another exemplary anterior glenoid guide 200 (arthroscopic anterior glenoid guide 200; graft guide 200; construct 200; surgical construct 200; guide 200; jig 200). FIGS. 17-20 illustrate various views of another exemplary anterior glenoid guide 300 (arthroscopic anterior glenoid guide 300; graft guide 300; construct 300; surgical construct 300; guide 300; jig 300). FIGS. 21 and 22 illustrate steps of an exemplary method of reconstructive surgery with the anterior glenoid guide of FIG. 5. FIGS. 23-27 illustrate steps of another exemplary method of reconstructive surgery with the anterior glenoid guide of FIG. 5. FIGS. 28-38 illustrate steps of additional exemplary methods of reconstructive surgery with anterior glenoid guides of the present disclosure and various fixation devices.

Anterior glenoid guide 100 of FIGS. 1-11 comprises a body 10 having a general cuboid shape, i.e., a three-dimensional solid body with six sides or faces (facets) that are all positioned at about 90 degrees angles relative to each other. In an exemplary embodiment, body 10 of anterior glenoid guide 100 is a cuboid block with a length L, a width W, a height H and a center C (FIG. 5), having exemplary dimensions of about 2×1×0.5 cm, dimensions which allow the construct to be introduced via the rotator interval and rest on the anterior glenoid, as detailed below.

Figure 1:
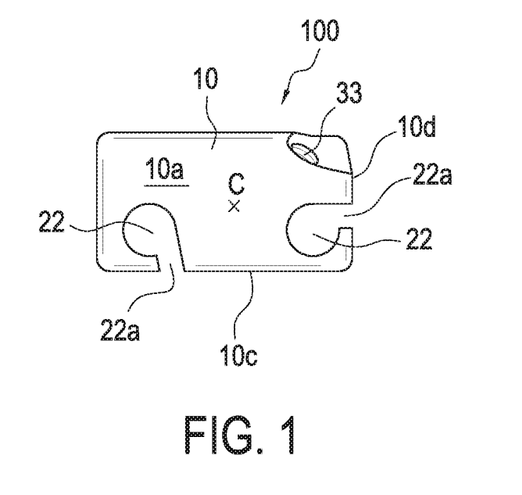
FIGS. 1-4 illustrate various views of an exemplary anterior glenoid guide.
Figure 2:
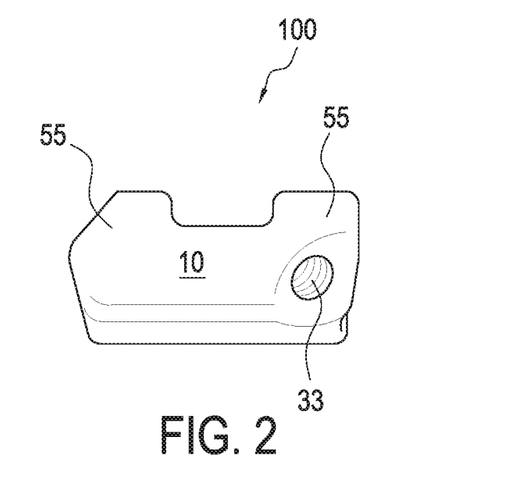
Figure 3:
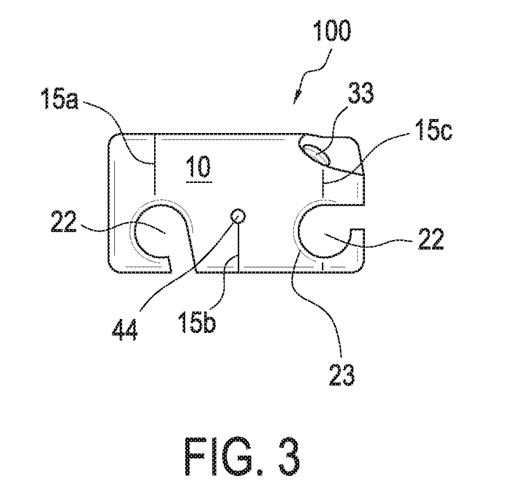
Figure 4:
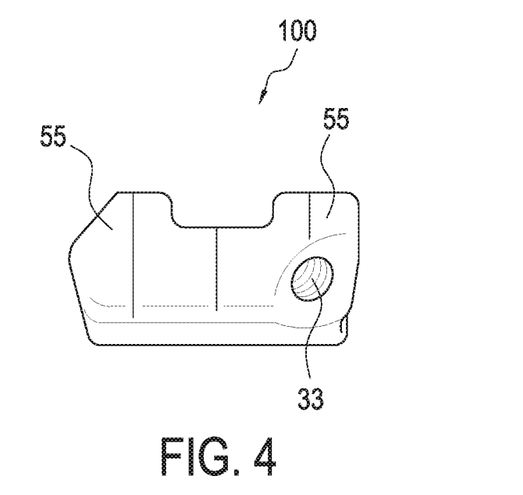
Figure 5:
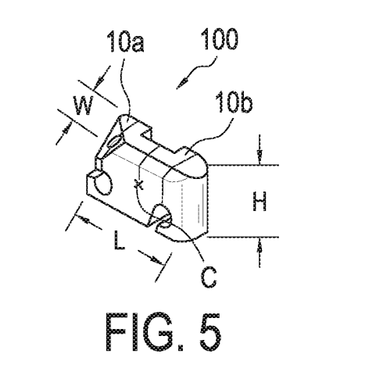
FIG. 5 is a perspective view of the anterior glenoid guide of FIGS. 1-4.
Figure 6:
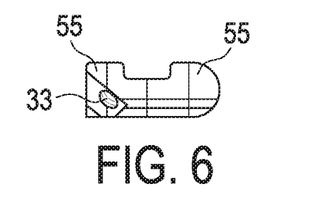
FIG. 6 is a top view of the anterior glenoid guide of FIG. 5.
Figure 7:
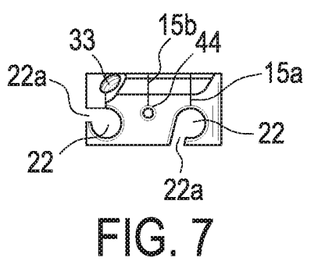
FIG. 7 is a front view of the anterior glenoid guide of FIG. 5.
Figure 8:
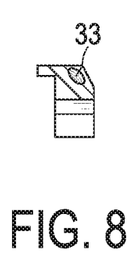
FIG. 8 is a right-side view of the anterior glenoid guide of FIG. 5.
Figure 9:
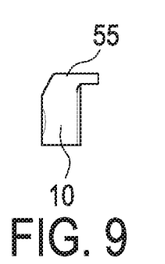
FIG. 9 is a left-side view of the anterior glenoid guide of FIG. 5.
Figure 10:
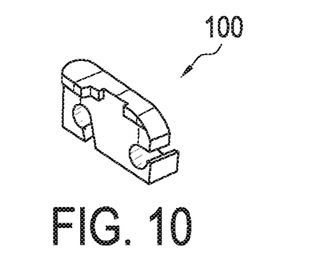
FIG. 10 is another perspective view of the anterior glenoid guide of FIG. 5 (rotated about 180 degrees).
Figure 11:
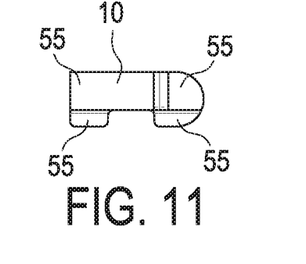
FIG. 11 is a top view of the anterior glenoid guide of FIG. 10.

As more clearly illustrated in FIGS. 5-11, anterior glenoid guide 100 includes a plurality of through-holes or apertures 22, extending from a first surface or side 10a of the body 10 to a second, opposite surface or side 10b of the body 10. Each hole 22 communicates with a surface or side of the construct through aperture 22a (opening 22a). In one embodiment, and as illustrated in FIG. 1., for example, apertures 22a are located on two different and adjacent surfaces/facets 10c and 10d of the body 10. Through-holes 22 are configured to allow engagement with, and passage of, one or more instruments, for example, drills or any cutting instruments during a drilling procedure. Through-holes 22 can be open ended bores (for example, cylindrically shaped and longitudinally extending) provided about parallel to each other and for receiving one or more instruments (for example, a drill guide and/or a drill) during use. Through-holes 22 may be provided with chamfered edges 23 (FIG. 3). Each of through-holes 22 of body 10 communicates with three separate facets or side surfaces of the body 10 (for example, facets 10a, 10b, 10c or 10a, 10b, 10d). Through-holes 22 can be symmetrically located relative to center C of the cuboid body. At least one or all of through-holes 22 can have internal threading for receiving one or more instruments, to guarantee the fixation devices drill guide instruments are parallel to the anterior guide.

Body 10 is also provided with a plurality of bone engaging structures 55 or flanges 55 (shown in FIGS. 2, 4 and 6, for example) and a K-wire hole 44 (for example, a 1.6 mm K-wire hole) as shown in FIG. 3, for example. Flanges 55 lie on the anterior side of the glenoid, for example, on the anterior rim of the glenoid. In an exemplary embodiment, the anterior glenoid guide is introduced via the rotator interval to rest on the anterior glenoid by engagement of flanges 55 with the rim of the glenoid. Laser lines 15a, 15b, 15c can be provided on the body 10 to pass through and indicate a center of holes 22, 44, as shown for example in FIGS. 3, 4 and 7.

Body 10 also includes a connecting structure 33 for engaging handle 76 (FIGS. 1-4 and 13-16). In an exemplary embodiment, connecting structure 33 is an internal thread that allows secure engagement to the handle. Internal thread 33 can be provided to extend from a slanted surface of the cuboid body 10 and into the body 10, and an angle relative to all three axis of the cuboid body 10, to allow easy handling of the anterior glenoid guide into the arthroscopic portal. In an embodiment, the angle can be of about 45 degrees.

FIG. 12 illustrates a surgical assembly with exemplary anterior glenoid guides 100 and associated drivers 70. Anterior glenoid guides 100 may be provided for both left and right shoulders, depending on the intended application and surgical needs.

FIGS. 13-20 illustrate various views of exemplary anterior glenoid guide 200, 300. Anterior glenoid guides 200, 300 are about similar to anterior glenoid guide 100 detailed above but differ in the position and orientation of through-holes 122. Through-holes 122 have the openings or apertures 122a located both on a same side/facet/surface 10c of the body 10 and not on two adjacent sides, as in the previously detailed embodiment.

Anterior glenoid guides 100, 200, 300 have applicability to various open and arthroscopic procedures, with particular application to arthroscopic anterior glenoid graft insertion. The novel guide enables simple positioning of the graft suture anchors from an anterior portal, eliminating the need for additional posterior incisions.

Reference is now made to FIGS. 21 and 22. FIG. 21 illustrates a partial view of a repair site 101 with exemplary anterior glenoid guide 100 passed through the rotator interval and placed on the anterior rim 80 of glenoid 90. FIG. 22 illustrates an anchor drill guide passed percutaneously through the subscapularis muscle and inserted into a hole of the anterior glenoid guide. An anchor specific drill is then used to drill across and parallel to the glenoid 90. A fixation device (such as an exemplary suture anchor 66) is then inserted into the guide with instrument 71. This step is conducted twice, through the superior and the inferior holes of the anterior guide (through separate incisions) (through the same anterior incision and subscapularis incision) to allow insertion and fixation of two fixation devices (such as two suture anchors 66). Both options are available, i.e., through the same incision or separate.

A sequence of surgical steps of an exemplary arthroscopic anterior glenoid grafting (using exemplary iliac crest) in an all-anterior approach with suture anchor stabilization and employing any of anterior glenoid guides 100, 200, 300 is set forth below:

1. Make an arthroscopic incision in the rotator interval;
2. Release the soft tissues from the anterior glenoid neck;
3. Debride the anterior glenoid neck with a burr or power rasp to create a flat surface 91 for grafting;
4. Introduce arthroscopic anterior glenoid guide 100, 200, 300 through the rotator interval;
5. Place flanges 55 flat against the articular surface with the anterior glenoid guide 100, 200, 300 held securely on the prepared anterior glenoid neck 80;
6. Pass a 1.6 mm K-wire through subscapularis and then through the anterior glenoid guide 100, 200, 300 (through hole 44) to provide temporary stabilization against the glenoid neck;
7. Insert the percutaneous dilator set through the subscapularis into the inferior hole in the anterior glenoid guide 100, 200, 300;
8. Pass the drill guide over the dilator and seat it in the inferior hole of the anterior glenoid guide (alternatively, the superior hole can be used first and then the inferior one);
9. Drill a bicortical hole through the drill guide. Remove the drill and leave the guide in place in the anterior glenoid guide 100, 200, 300;
10. Insert a FiberTak® RC anchor 66 through the guide and pass it bicortically;
11. Remove the drill guide from anterior glenoid guide 100, 200, 300 but leave it within the joint;
12. Remove the anchor sutures 68 via a second incision in rotator interval;
13. Insert the drill guide into the superior hole of the anterior glenoid guide;
14. Drill bicortically and insert the FiberTak® RC anchor 66;
15. Remove the drill guide;
16. Remove the anchor sutures 68 through the second rotator interval incision;
17. Remove the anterior glenoid guide 100, 200, 300 then from the joint through the rotator interval;
18. Retrieve the anchor sutures 68 together via the initial rotator interval incision;
19. Pass the anchor sutures 68 through graft outside body, inferior sutures 68 through the inferior graft hole, superior sutures 68 through the superior graft hole;
20. Pass the sutures passed through two-hole plate. For each paired suture pass one limb inside plate, one limb outside;
21. Reload the graft and plate down sutures to lie on the anterior glenoid 90;
22. Load the ACL tensioner onto one pair of the inferior sutures 68 (one inside and one outside the plate);
23. Use the ACL tensioner to tension the sutures to about 80N;
24. Tie the second suture pair from the same anchor 66;
25. Repeat the process for one pair from the superior anchor; and
26. Tie the other suture pairs independently.

Graft Preparation

1. Cut the desired size of exemplary tricortical iliac crest graft (or other graft) (graft material);
2. Place the anterior glenoid guide 100, 200, 300 on the anterior surface of the graft material;
3. Secure the anterior glenoid guide with the 1.6 mm K-wire; and
4. Drill two holes through the graft material using the drill guide and drill, to form a graft employed for subsequent grafting.

FIGS. 23-27 illustrate subsequent steps of arthroscopic anterior graft placement repair in shoulder surgery at surgical site 101 with exemplary anterior glenoid guide 100.

The anterior glenoid guide for arthroscopic glenoid grafting is employed from front to back (and not back to front like the current guides). The flanges 55 allow the guide 100, 200, 300 to lie about flat on the glenoid neck. The fixation is conducted by using sutures 68 and, therefore, they do not need to be parallel to each other. The depth of the anterior glenoid guide 100, 200, 300 keeps the construct (drill guide) in a stable position. Various fixation devices in the form of screws, buttons, suture-button constructs, anchors, soft suture anchors (such as knotted and knotless suture anchors) and plates, among many others, can be employed with the anterior glenoid guide 100, 200, 300. As detailed above, suture constructs such as TightRope® 66 or all-suture anchors 66 can be employed with associated sutures 68 for arthroscopic glenoid grafting and fixation. FIGS. 28-38 described below illustrate additional fixation devices such as screws and/or suture-button constructs employed with any of the anterior glenoid guides 100, 200, 300.

Figures 28, 29, 30:
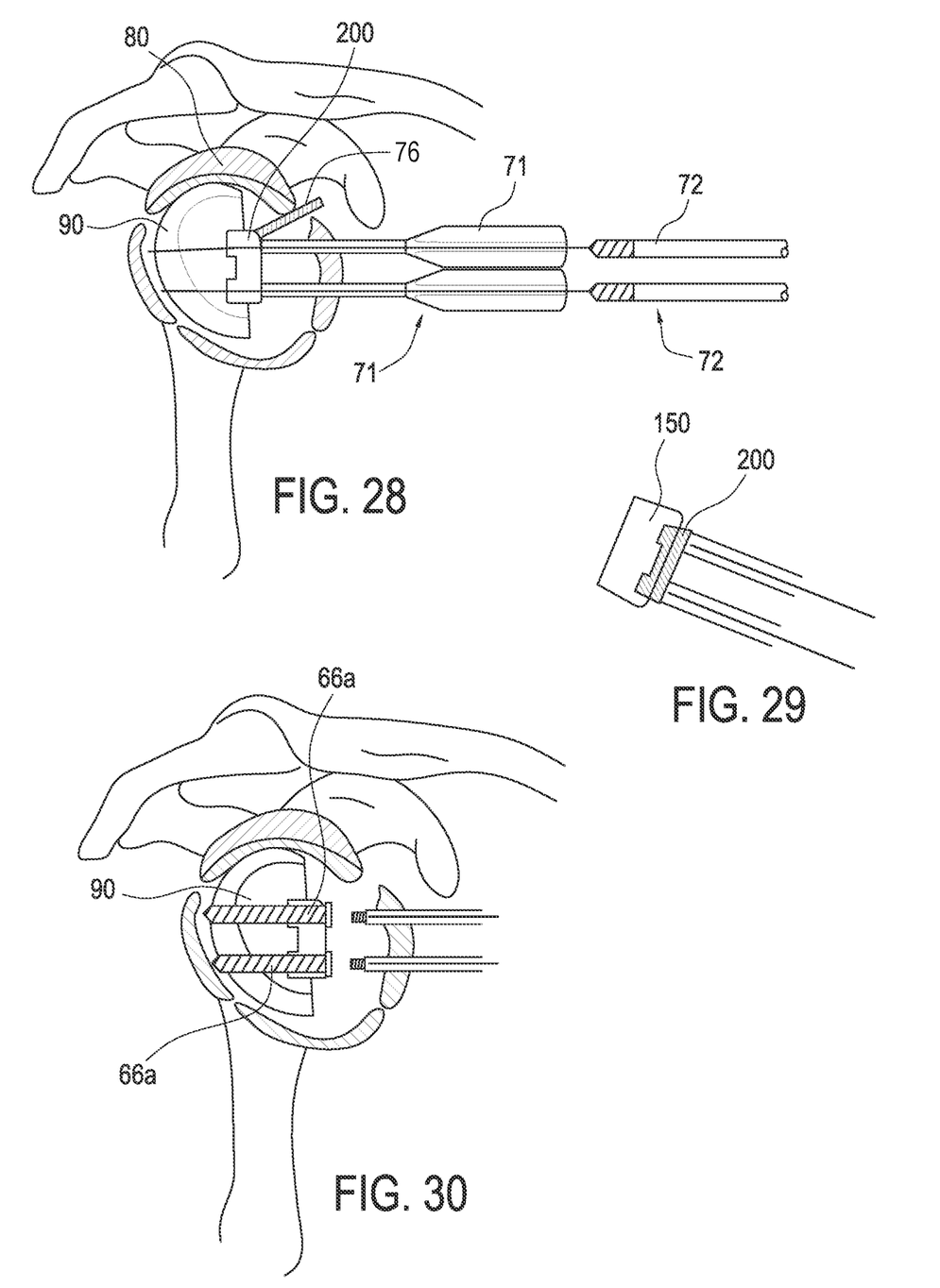
FIGS. 28-30 illustrate steps of another exemplary method of reconstructive surgery with an anterior glenoid guide and screw fixation.

FIGS. 28-30 illustrate subsequent steps of an exemplary method of reconstructive surgery with any of anterior glenoid guides 100, 200, 300 and screw fixation. FIG. 28 illustrates exemplary anterior glenoid guide 200 on glenoid 90. Drill guide with inner sleeve to help accurately drill K-wires through the glenoid until posterior cortex exit. Overdrill with cannulated drills 72 (size is necessary for screw insertion). FIG. 29 shows drilling of holes in bone block 150 or coracoid 150 using anterior glenoid guide 200. Slide the bone block 150 over the K-wires (FIG. 30) until flush with the anterior glenoid. Insert screws 66a through sleeves. Screws 66a can be interference screws.

Figures 31, 32, 33, 34:
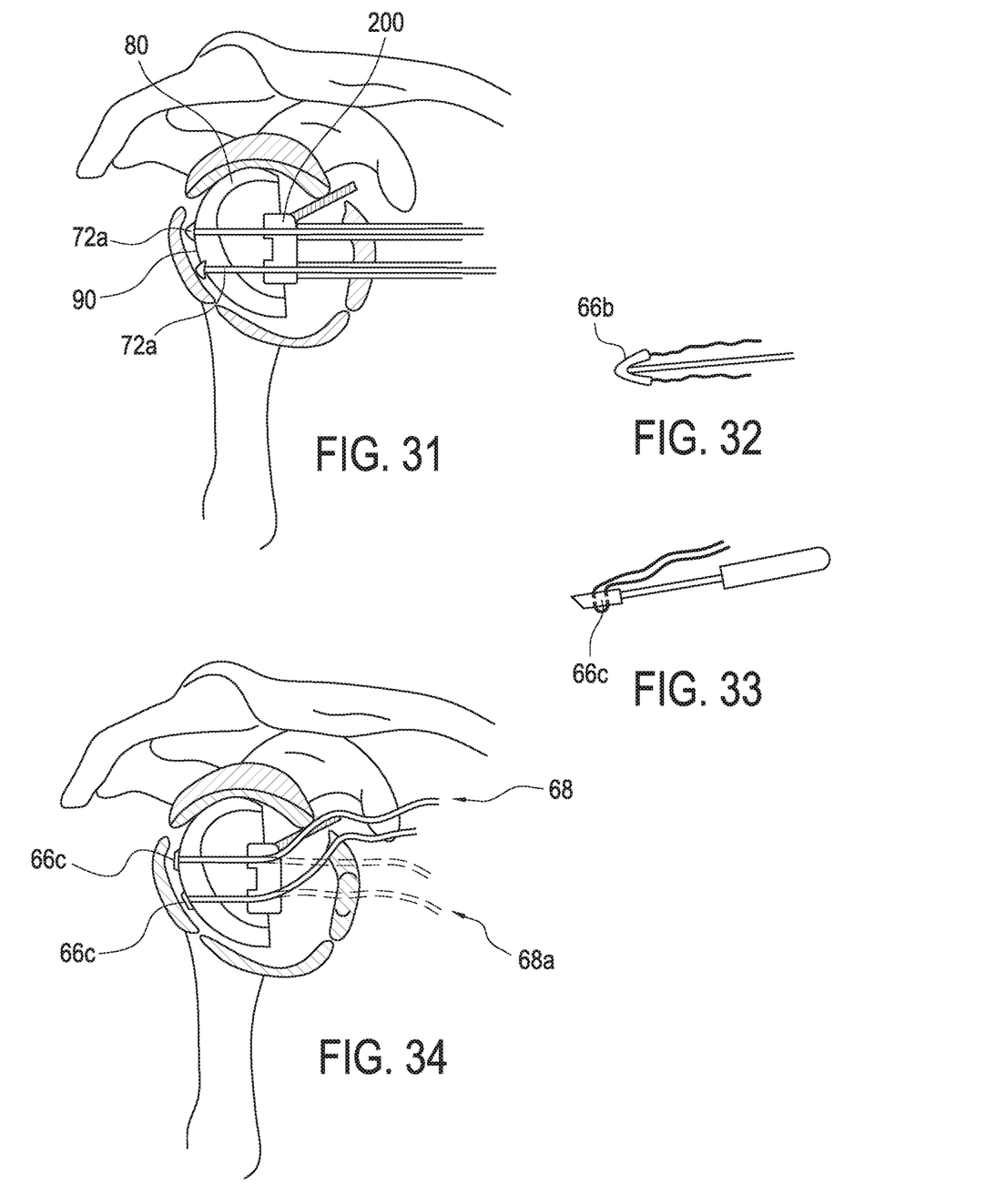
FIGS. 31-34 illustrate steps of another exemplary method of reconstructive surgery with an anterior glenoid guide and suture/button fixation.

FIGS. 31-34 illustrate subsequent steps of an exemplary method of reconstructive surgery with any of anterior glenoid guides 100, 200, 300 and suture/button fixation. FIG. 31 illustrates exemplary anterior glenoid guide 200 positioned on glenoid 90. Drill spade tip 72a through the posterior cortex for buttons; alternatively, drill with a specific bicortical anchor drill. FIG. 32 illustrates a FiberTak® suture anchor/bicortical suture button 66b (suture-button construct 66b). FIG. 33 illustrates an exemplary cortical button 66c with suture attached. The sutures can be different, for example, FiberWire® suture, TigerWire® suture, FiberTape® suture tape, or any flexible suture material or combination thereof. Insert the cortical button 66c with suture attached and fix the button bicortically. The button can be formed of any material such as metal, metal alloy, plastic, suture, or combinations thereof. FIG. 34 depicts sutures 68 retrieved through rotator interval when using a bone block, and sutures 68a (shown in dotted lines) retrieved through subscapularis when using coracoid.

Figure 35:
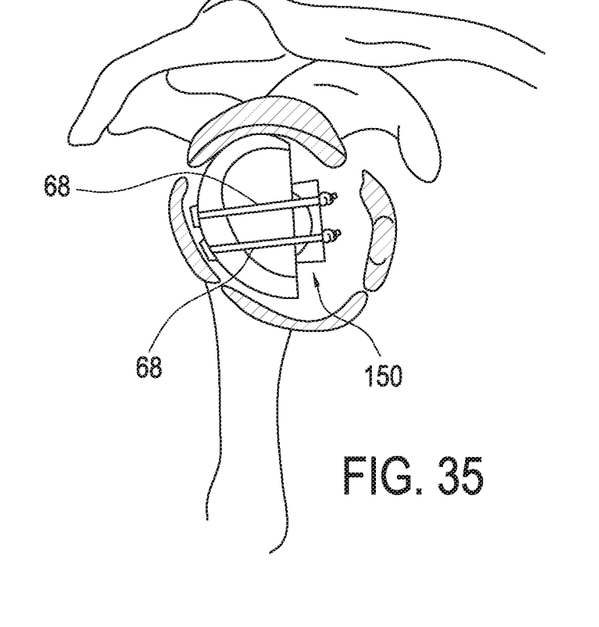
FIGS. 35-38 illustrate steps of another exemplary method of reconstructive surgery with an anterior glenoid guide and suture fixation configurations.
Figure 36:
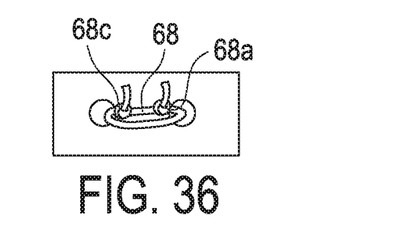
Figure 37:
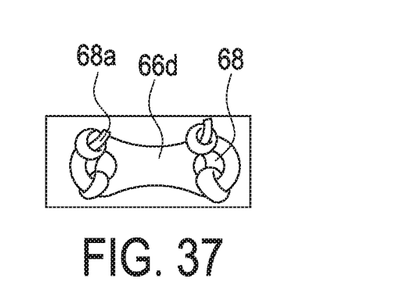
Figure 38:
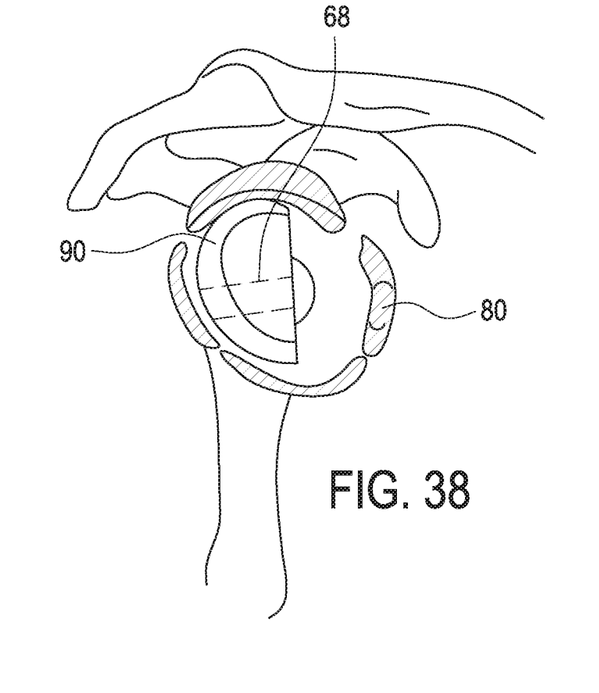

FIGS. 35-38 illustrate subsequent steps of an exemplary method of reconstructive surgery with any of anterior glenoid guides 100, 200, 300 and suture fixation configurations. FIGS. 35 and 38 show sutures 68 passed through bone block or coracoid 150, then inserted through rotator interval of subscapularis. FIG. 36 depicts sutures 68 interconnected in a manner similar to that used in a boneblock cerclage technique, either using a plate or without, and with a knotless construct or interconnected knots 68*a*. FIG. 37 illustrates suture 68 knotted to plate 66*d* and tensioned.

The anterior glenoid guide 100, 200, 300 is a cuboid guide provided with specific dimensions and employed in an anterior-to-posterior manner from front to back (and not back to front like the current guides), and with flanges 55 that allow the guide to lie flat on the glenoid neck 80 and with holes 22, 122 to allow a drill guide and sutures with or without fixation devices to pass therethrough.

The flexible strands 68 can be formed of any flexible material such as suture or tape, or combination of suture and tape. The suture may be in the form of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). The tape may be formed of suture tape, for example, Arthrex FiberTape®, which is a high strength suture tape that is braided and rectangular-like in cross section and as disclosed in U.S. Pat. No. 7,892,256, the disclosure of which is hereby incorporated by reference in its entirety herein.

Anterior glenoid guides 100, 200, 300 described above can be included in a surgical kit, assembly, or system to simplify the surgeon's task of selecting a specific instrument and to aid in the overall surgical procedure. A surgical kit for an arthroscopic surgical repair may include one or more guides 100, 200, 300 and an obturator sized for use with the guide(s) 100, 200, 300. The surgical kit may include awls or equivalent devices, as well as drills or bone-penetrating devices. The surgical kit may also include a tensioner and/or bone plates and associated instrumentation. The surgical kit may include fixation devices (such as anchors 66, screws 66*a*, suture-button constructs 66*b*, 66*c*, plates 66*d*, etc.) and flexible members (such as sutures 68) to be employed in conjunction with the bone tunnels, bores or holes formed by the anterior glenoid guide 100, 200, 300.

In an exemplary embodiment, the fixation device can be an all-suture soft anchor (soft suture anchor) provided with a soft anchor sleeve (sheath, tubular member) with two open ends and one or more flexible shuttling strands extending through the soft anchor sleeve (sheath). The at least two flexible strands may extend through the sleeve in similar or different directions and/or orientations and/or locations. The flexible sleeve with the one or more shuttling strands is secured into or onto bone, and the strands allow passing of additional flexible strands such as tapes to pass over soft tissue and be secured into bone to approximate soft tissue to bone. Details of an exemplary soft suture anchor with a soft anchor sleeve (sheath or tubular member) and flexible shuttling strands are set forth, for example, in U.S. application Ser. No. 15/998,516 entitled "Methods of Tissue Repairs" filed on Aug. 16, 2018, the disclosure of which is incorporated by reference in its entirety herein.

Anterior glenoid guides 100, 200, 300 detailed above are graft guides with applicability to various open or arthroscopic procedures including procedures for re-approximating bone to bone or soft tissue to bone, for example, shoulder rotator cuff repairs, capsulolabral reconstruction, SLAP repairs, as well as ankle, knee, elbow or foot repairs. Guides 100, 200, 300 have particular application to arthroscopic shoulder repairs conducted in an anterior manner, from anterior-to-posterior and not from posterior-to-anterior.

An anterior glenoid guide 100, 200, 300 can be an arthroscopic anterior glenoid guide 100, 200, 300. An anterior glenoid guide 100, 200, 300 can be introduced in an anterior-to-posterior way from front to back, and not from back to front. In an embodiment, an anterior glenoid guide 100, 200, 300 can be introduced arthroscopically via the rotator interval and positioned to rest on the anterior glenoid 90. An anterior glenoid guide 100, 200, 300 can include a body 10 in the shape of a general cuboid provided with a plurality of flanges 55 that allow positioning on an anterior face 91 of the bone 90 (e.g., the glenoid); a thread 33 to accommodate a handle 76; and a plurality of through-holes 22, 122 or apertures 22, 122 that are configured and sized to engage a drill guide and allow easy passage of flexible members 68 (such as sutures or suture tapes 68) from fixation devices 66 used for graft fixation. An anterior glenoid guide 100, 200, 300 can be positioned onto the anterior face of a bone (glenoid) by secure engagement of the bone with a plurality of flanges 55. The guide 100, 200, 300 is a simple construct that allows precise, accurate and convenient positioning on an anterior face of a bone 90 to be grafted (e.g., an anterior face of the glenoid). The anterior glenoid guide 100, 200, 300 eliminates the posterior insertion of instrumentation necessary for reconstruction surgeries such as open rotator cuff reconstruction (e.g., guides inserted posteriorly and through the back of the glenoid) as well as posterior incisions. The guide 100, 200, 300 of the present disclosure also allows precise and fast placement of a graft onto a bone to be grafted without additional incisions and unnecessary drilling of bone tunnels through the bone to be grafted, as well as improved suture management at the repair site.

Methods of endoscopic or arthroscopic surgeries are also disclosed. An exemplary method includes inter alia the steps of: (i) arthroscopically positioning an anterior glenoid guide 100, 200, 300 on an anterior face of a bone 90; and (ii) securing a surgical instrument 70, 71, 76 to the anterior glenoid guide 100, 200, 300. The bone 90 can be the glenoid. The method further includes the steps of: introducing the anterior glenoid guide 100, 200, 300 through an anterior arthroscopic portal and into a vicinity of the bone 90; engaging a plurality of bone engaging structures 55 (flanges 55) of the anterior glenoid guide 100, 200, 300 with one or more bone surfaces 91 of the bone 90; and drilling into the bone 90. In an embodiment, drilling can occur from one surface 91 of the bone to another surface of the bone (for example, an opposite surface) to form one or more through-tunnels or holes. In an embodiment, drilling can occur from one surface of the bone to another surface of the bone, to form two through-tunnels spaced apart from each other and about parallel to each other.

The method can further include the steps of: placing the anterior glenoid guide 100, 200, 300 on a surface of a graft material; securing the anterior glenoid guide 100, 200, 300 to the graft material; and drilling into the graft material to form a graft 150 with two through tunnels. The anterior glenoid guide 100, 200, 300 can be an arthroscopic anterior glenoid guide in the shape of a cuboid employed for glenoid grafting in an anterior-to-posterior manner.

What is claimed is:
1. An anterior glenoid guide comprising:
a body in a shape of a cuboid with a length, a width and a height;
a plurality of flanges adapted to engage an anterior surface of a glenoid to be grafted; and
two through-holes extending from a first surface of the cuboid body to a second surface of the body in the shape of the cuboid, wherein each of the two through-holes communicates with three separate facets or side surfaces of the body.

2. The anterior glenoid guide of claim 1, wherein the plurality of flanges consists of two flanges that engage an anterior neck of the glenoid.

3. The anterior glenoid guide of claim 1, wherein the body in the shape of the cuboid further comprises a plurality of laser lines that reference a center of each of the plurality of the through-holes.

4. The anterior glenoid guide of claim 1, wherein the length is about 2 cm, the width is about 1 cm, and the height is about 0.5 cm.

5. The anterior glenoid guide of claim 1, wherein the two through-holes are symmetrically located relative to a center of the cuboid body.

6. The anterior glenoid guide of claim 1, wherein the body in the shape of the cuboid further comprises an internal thread configured to securely engage a handle.

7. The anterior glenoid guide of claim 1, wherein the anterior glenoid guide is employed in arthroscopic shoulder surgery conducted in an anterior-to-posterior manner.

8. A surgical kit, comprising:
an anterior glenoid guide comprising a solid body in a shape of a cuboid with a width, a length and a height; two flanges adapted to engage an anterior surface of a glenoid to be drilled; two through-holes extending from a first surface of the cuboid body to a second surface of the solid body in the shape of the cuboid, wherein each of the two through-holes communicates with three separate facets or side surfaces of the solid body; and an internal thread configured to engage a handle; and
an obturator.

9. The surgical kit of claim 8, further comprising at least one cutting instrument.

10. The surgical kit of claim 8, further comprising at least one fixation device.

11. The surgical kit of claim 10, wherein the at least one fixation device is a soft suture anchor comprising a flexible tubular sleeve or sheath and a plurality of flexible strands extending through a passage of the flexible tubular sleeve or sheath.

* * * * *